(12) United States Patent
Wang et al.

(10) Patent No.: US 12,343,882 B2
(45) Date of Patent: Jul. 1, 2025

(54) AUTOMATIC COLLIMATOR INSTALLATION SYSTEMS AND METHODS

(71) Applicant: SHANGHAI UNITED IMAGING HEALTHCARE CO., LTD., Shanghai (CN)

(72) Inventors: Beien Wang, Shanghai (CN); Li Fang, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 431 days.

(21) Appl. No.: 18/052,945

(22) Filed: Nov. 7, 2022

(65) Prior Publication Data

US 2023/0142017 A1 May 11, 2023

(30) Foreign Application Priority Data

Nov. 8, 2021 (CN) .......................... 202111315533.5

(51) Int. Cl.
*A61B 6/06* (2006.01)
*A61B 6/00* (2006.01)
*B25J 9/16* (2006.01)
*B65G 1/137* (2006.01)
*A61B 90/98* (2016.01)

(52) U.S. Cl.
CPC ............... *B25J 9/1687* (2013.01); *A61B 6/06* (2013.01); *A61B 6/4411* (2013.01); *A61B 6/4494* (2013.01); *B65G 1/137* (2013.01); *A61B 90/98* (2016.02)

(58) Field of Classification Search
CPC ........ B25J 9/1687; A61B 6/06; A61B 6/4411; A61B 6/4494; A61B 90/98; B65G 1/137
See application file for complete search history.

*Primary Examiner* — Mathew Franklin Gordon
(74) *Attorney, Agent, or Firm* — METIS IP LLC

(57) ABSTRACT

The present disclosure is related to automatic collimator installation systems and methods. An automatic collimator installation method may include obtaining an installation instruction for installing a target collimator into a medical scanner; identifying, from a plurality of collimators stored in a collimator storage device, the target collimator based on the installation instruction; using a cart to transport the target collimator from the collimator storage device to the medical scanner; and automatically installing, using the cart, the target collimator into the medical scanner.

20 Claims, 9 Drawing Sheets

1100

Automatically uninstalling, using a cart, an installed collimator from a medical scanner based on an installation instruction — 1110

Using the cart to transport the installed collimator from the medical scanner to a collimator storage device — 1120

Obtaining a scan protocol — 1210

Determining an installation instruction based on the scan protocol — 1220

FIG. 12

AUTOMATIC COLLIMATOR INSTALLATION SYSTEMS AND METHODS

CROSS-REFERENCE TO RELATED APPLICATIONS

This application claims priority of Chinese Patent Application No. 202111315533.5, filed on Nov. 8, 2021, the contents of which are hereby incorporated by reference.

TECHNICAL FIELD

This disclosure generally relates to collimator technology, and more particularly, relates to automatic collimator installation systems and methods.

BACKGROUND

Nuclear medicine functional imaging techniques (e.g., single-photon emission computed tomography (SPECT)) are widely used in medical diagnosis. A SPECT device generally has a plurality of different collimators for positioning different radioactive tracers. However, the plurality of collimators are usually manually installed or uninstalled, which wastes a lot of time and manpower. Thus, it is desirable to develop automatic collimator installation systems and methods.

SUMMARY

According to an aspect of the present disclosure, an automatic collimator installation system is provided. The system may include a cart, a storage medium including a set of instructions, and at least one processor configured to communicate with the storage medium. When executing the set of instructions, the at least one processor is configured to direct the system to perform operations including:

In some embodiments, the using the cart to transport the target collimator from the collimator storage device to the medical scanner may include: using the cart to transport, based on a predetermined route, the target collimator from the collimator storage device to a predetermined location of the medical scanner; and using the cart to align, based on a navigation algorithm, the target collimator with a detector of the medical scanner.

In some embodiments, the navigation algorithm may include at least one of: a laser navigation algorithm, a visual navigation algorithm, or an inertial navigation algorithm.

In some embodiments, the automatically installing, by the cart, the target collimator into the medical scanner may include: automatically installing, by a locating module of the cart, the target collimator onto a detector of the medical scanner.

In some embodiments, the locating module includes a locating hole or a locating pin.

In some embodiments, the identifying, from the plurality of collimators stored in the collimator storage device, the target collimator based on the installation instruction may include: obtaining a target identifier of the target collimator based on the installation instruction; identifying a plurality of identifiers respectively corresponding to the plurality of collimators; and identifying the target collimator by matching the target identifier with one of the plurality of identifiers respectively corresponding to the plurality of collimators.

In some embodiments, the plurality of identifiers of the plurality of collimators may be identified according to at least one of: a mechanical switch, a proximity switch, a photoelectric switch, an electromagnetic sensor, a radiofrequency identification tag, or a unique symbol.

In some embodiments, the operations may further include: automatically uninstalling, using the cart, an installed collimator from the medical scanner based on the installation instruction; and using the cart to transport the installed collimator from the medical scanner to the collimator storage device.

In some embodiments, the target collimator may include at least one of: a pinhole collimator, a parallel hole collimator, a fan-beam collimator, a cone-beam collimator, or a slit-slat collimator.

In some embodiments, the automatic collimator installation system may further comprise the collimator storage device configured to store the plurality of collimators, and the collimator storage device is away from the medical scanner.

In some embodiments, the operations may further include: obtaining a scan protocol; and determining the installation instruction based on the scan protocol.

According to another aspect of the present disclosure, a cart may include a mechanical arm, a cart body, a processor, and a storage medium including a set of instructions. The processor may be configured to communicate with the storage medium. when executing the set of instructions, the processor may be configured to direct the cart to perform operations including: obtaining an installation instruction for installing a target collimator into a medical scanner; identifying, from a plurality of collimators stored in a collimator storage device, the target collimator based on the installation instruction; griping, using the mechanical arm, the target collimator from the collimator storage device to the cart body; controlling the cart body to transport the target collimator from the collimator storage device to the medical scanner; and automatically installing, using the mechanical arm, the target collimator into the medical scanner.

According to another aspect of the present disclosure, an automatic collimator installation method may include obtaining an installation instruction for installing a target collimator into a medical scanner; identifying, from a plurality of collimators stored in a collimator storage device, the target collimator based on the installation instruction; using a cart to transport the target collimator from the collimator storage device to the medical scanner; and automatically installing, using the cart, the target collimator into the medical scanner.

According to still another aspect of the present disclosure, a non-transitory computer readable medium may include at least one set of instructions. When executed by at least one processor of a computing device, the at least one set of instructions may cause the at least one processor to effectuate a method. The method may include obtaining an installation instruction for installing a target collimator into a medical scanner; identifying, from a plurality of collimators stored in a collimator storage device, the target collimator based on the installation instruction; using a cart to transport the target collimator from the collimator storage device to the medical scanner; and automatically installing, using the cart, the target collimator into the medical scanner.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein:

FIG. 11 is a flowchart illustrating an exemplary process for uninstalling an installed collimator according to some embodiments of the present disclosure; and FIG. 12 is a flowchart illustrating an exemplary process for determining an installation instruction according to some embodiments of the present disclosure.

DETAILED DESCRIPTION

Figure 1:
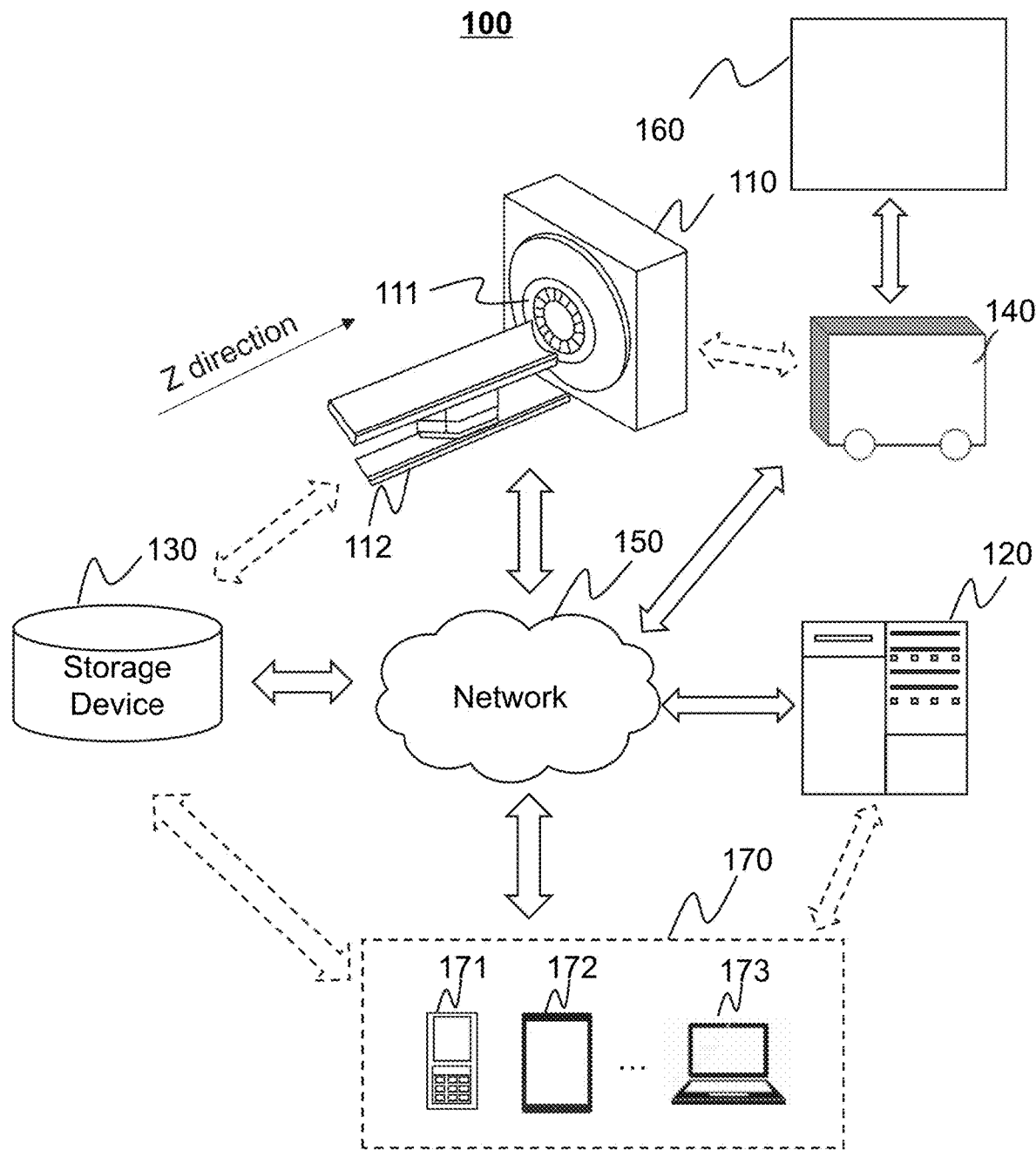
FIG. 1 is a schematic diagram illustrating an exemplary automatic collimator installation system according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. Also, the term "exemplary" is intended to refer to an example or illustration.

It will be understood that the terms "system," "engine," "unit," "module," and/or "block" used herein are one method to distinguish different components, elements, parts, sections or assembly of different levels in ascending order. However, the terms may be displaced by another expression if they achieve the same purpose.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that, although the terms "first," "second," "third," etc., may be used herein to describe various elements, these elements should not be limited by these terms. These terms are only used to distinguish one element from another. For example, a first element could be termed a second element, and, similarly, a second element could be termed a first element, without departing from the scope of exemplary embodiments of the present disclosure.

Spatial and functional relationships between elements are described using various terms, including "connected," "attached," and "mounted." Unless explicitly described as being "direct," when a relationship between first and second elements is described in the present disclosure, that relationship includes a direct relationship where no other intervening elements are present between the first and second elements, and also an indirect relationship where one or more intervening elements are present (either spatially or functionally) between the first and second elements. In contrast, when an element is referred to as being "directly" connected, attached, or positioned to another element, there are no intervening elements present. Other words used to describe the relationship between elements should be interpreted in a like fashion (e.g., "between," versus "directly between," "adjacent," versus "directly adjacent," etc.).

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The term "image" in the present disclosure is used to collectively refer to image data (e.g., scan data, projection data) and/or images of various forms, including a two-dimensional (2D) image, a three-dimensional (3D) image, a four-dimensional (4D), etc. The term "pixel" and "voxel" in the present disclosure are used interchangeably to refer to an element of an image. The term "anatomical structure" in the present disclosure may refer to gas (e.g., air), liquid (e.g., water), solid (e.g., stone) cell, tissue, organ of a subject, or any combination thereof, which may be displayed in an image and really exist in or on the subject's body. The term "region," "location," and "area" in the present disclosure may refer to a location of an anatomical structure shown in the image or an actual location of the anatomical structure existing in or on the subject's body, since the image may indicate the actual location of a certain anatomical structure existing in or on the subject's body. The term "an image of a subject" may be referred to as the subject for brevity.

For illustration purposes, the following description is provided to help better understanding an image registration process. It is understood that this is not intended to limit the scope of the present disclosure. For persons having ordinary skills in the art, a certain amount of variations, changes and/or modifications may be deducted under the guidance of the present disclosure. Those variations, changes and/or modifications do not depart from the scope of the present disclosure.

An aspect of the present disclosure relates to automatic collimator installation systems and methods. As used herein, the word "automatically" or "automatic" may refer that a process is performed in a mechanical manner without any human assistance. In some embodiments, the systems and methods may identify, from a plurality of collimators stored in a collimator storage device, a target collimator based on an installation instruction. The systems and methods may use a cart to transport the target collimator from the collimator storage device to a medical scanner (e.g., a SPECT device, a CT-SPCT device, etc.), and automatically install, using the cart, the target collimator into the medical scanner. In some embodiments, the cart may automatically identify the target collimator by matching a target identifier of the target collimator with one of the plurality of identifiers respectively corresponding to the plurality of collimators. The cart may transport the target collimator from the collimator storage device to a predetermined location of the medical scanner based on a predetermined route. The cart may align, based on a navigation algorithm (e.g., a laser navigation algorithm, a visual navigation algorithm, or an inertial navigation algorithm, etc.), the target collimator with a detector of the medical scanner. The cart may automatically install, by a locating module (e.g., a locating hole or a locating pin) of the cart, the target collimator onto a detector of the medical scanner. According to some embodiments of the present disclosure, the target collimator may be automatically identified, installed, or uninstalled without any human assistance. The accuracy of identifying the target collimator and the installation efficiency of collimators may be improved.

FIG. 1 is a schematic diagram illustrating an exemplary automatic collimator installation system 100 according to some embodiments of the present disclosure. As shown, the automatic collimator installation system 100 may include a medical device 110, a processing device 120, a storage device 130, a cart 140, a network 150, a collimator storage device 160, and one or more terminal(s) 170. In some embodiments, the medical device 110, the processing device 120, the storage device 130, the cart 140, the collimator storage device 160, and/or the terminal(s) 170 may be connected to and/or communicate with each other via a wireless connection (e.g., the network 150), a wired connection, or a combination thereof. The automatic collimator installation system 100 may include various types of connections between its components. For example, the medical device 110 may be connected to the processing device 120 through the network 150, or connected to the processing device 120 directly as illustrated by the bidirectional dotted arrow connecting the medical device 110 and the processing device 120 in FIG. 1. As another example, the cart 140 may be connected to the processing device 120 through the network 150, or connected to the processing device 120 directly as illustrated by the bidirectional dotted arrow connecting the cart 140 and the processing device 120 in FIG. 1. As still another example, the storage device 130 may be connected to the medical device 110 through the network 150, or connected to the medical device 110 directly as illustrated by the bidirectional dotted arrow connecting the medical device 110 and the storage device 130 in FIG. 1. As still another example, the storage device 130 may be connected to the cart 140 through the network 150, or connected to the cart 140 directly as illustrated by the bidirectional dotted arrow connecting the cart 140 and the storage device 130 in FIG. 1.

The medical device 110 may be configured to acquire imaging data relating to a subject. The imaging data relating to a subject may include an image (e.g., an image slice), projection data, or a combination thereof. In some embodiments, the imaging data may be a two-dimensional (2D) imaging data, a three-dimensional (3D) imaging data, a four-dimensional (4D) imaging data, or the like, or any combination thereof. The subject may be biological or non-biological. For example, the subject may include a patient, a man-made object, etc. As another example, the subject may include a specific portion, an organ, and/or tissue of the patient. Specifically, the subject may include the head, the neck, the thorax, the heart, the stomach, a blood vessel, soft tissue, a tumor, or the like, or any combination thereof. In the present disclosure, "object" and "subject" are used interchangeably.

In some embodiments, the medical device 110 may include a single modality imaging device. For example, the medical device 110 may include a single-photon emission computed tomography (SPECT) device, a positron emission tomography (PET) device, etc. In some embodiments, the medical device 110 may include a multi-modality imaging device. Exemplary multi-modality imaging devices may include a SPECT-CT device, a SPECT-PET device, a SPECT-MR device, etc. The medical device 110 may include a medical scanner 111 and a bed 112. A SPECT device may be taken as an example of the medical device 110, and not intended to limit the scope of the present disclosure. The medical scanner 111 of the SPECT device may include a gantry, a collimator, a detector, an electronics module, and/or other components not shown. The gantry may support one or more parts of the SPECT device, for example, the collimator, the detector, the electronics module, and/or other components. The collimator may collimate photons (e.g., y photons) emitted from an object being examined. The detector may be configured to detect the photons collimated by the collimator and/or generate electrical signals. The electronics module may collect and/or process electrical signals (e.g., scintillation pulses) generated by the detector. The electronics module may convert an analog signal (e.g., an electrical signal generated by the detector) relating to a photon detected by the detector to a digital signal to generate projection data. In some embodiments, the electronics module may be part of the detector. The bed 112 may be configured to support the object. In some embodiments, the bed 112 may move the object along a direction (e.g., Z direction shown in FIG. 1), so that the bed 112 may move into or out of the gantry of the medical device 110.

The processing device 120 may process data and/or information obtained from the medical device 110, the storage device 130, and/or the cart 140. For example, the processing device 120 may obtain an installation instruction for installing a target collimator into the medical scanner 111. As another example, the processing device 120 may identify, from a plurality of collimators stored in the collimator storage device 160, the target collimator based on the installation instruction. As still another example, the processing device 120 may use the cart 140 to transport the target collimator from the collimator storage device 160 to the medical scanner 111, and automatically install, using the cart, the target collimator into the medical scanner 111.

In some embodiments, the processing device 120 may be a single server or a server group. The server group may be centralized or distributed. In some embodiments, the processing device 120 may be local or remote. For example, the processing device 120 may access information and/or data from the medical device 110, the storage device 130, and/or the cart 140 via the network 150. As another example, the processing device 120 may be directly connected to the medical device 110, the cart 140, and/or the storage device 130 to access information and/or data. In some embodiments, the processing device 120 may be implemented on a cloud platform. For example, the cloud platform may include a private cloud, a public cloud, a hybrid cloud, a community cloud, a distributed cloud, an inter-cloud, a multi-cloud, or the like, or a combination thereof. In some embodiments, the processing device 120 may be part of the cart 140. In some embodiments, the processing device 120 may be part of the medical device 110.

The storage device 130 may store data, instructions, and/or any other information. In some embodiments, the storage device 130 may store data and/or instructions that the processing device 120, and/or the cart 140 may execute or use to perform exemplary methods described in the present disclosure. In some embodiments, the storage device 130 may include a mass storage, removable storage, a volatile read-and-write memory, a read-only memory (ROM), or the like, or any combination thereof. Exemplary mass storages may include a magnetic disk, an optical disk, a solid-state drive, etc. Exemplary removable storages may include a flash drive, a floppy disk, an optical disk, a memory card, a zip disk, a magnetic tape, etc. Exemplary volatile read-and-write memories may include a random-access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 130 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 130 may be connected to the network 150 to communicate with one or more other components in the automatic collimator installation system 100 (e.g., the processing device 120, the cart 140, etc.). One or more components in the automatic collimator installation system 100 may access the data or instructions stored in the storage device 130 via the network 150. In some embodiments, the storage device 130 may be integrated into the medical device 110 or the cart 140.

The cart 140 may be connected to and/or communicate with the medical device 110, the processing device 120, the storage device 130, and/or the collimator storage device 160. In some embodiments, the cart 140 may include a cart body, a mechanical arm, and wheels. In some embodiments, the cart 140 may include a mechanical arm, a cart body, wheels, a storage device, and a processor. The storage device may include a set of instructions, and when executing the set of instructions, the processor is configured to direct the cart to perform operations. The operations may include obtaining an installation instruction for installing a target collimator into a medical scanner; identifying, from a plurality of collimators stored in a collimator storage device, the target collimator based on the installation instruction; griping, using the mechanical arm, the target collimator from the collimator storage device to the cart body; controlling the cart body to transport the target collimator from the collimator storage device to the medical scanner; and automatically installing, using the mechanical arm, the target collimator into the medical scanner. In some embodiments, the cart body may be configured to support a collimator (e.g., a target collimator or an installed collimator) for transport between the medical device 110 and the collimator storage device 160. For example, the cart body may include a collimator platform and a driving mechanism mounted on the collimator platform. The collimator platform may be configured to support the collimator (e.g., the target collimator or the installed collimator). In some embodiments, the driving mechanism may be configured to communicate with the processing device 120 (or the processor) to receive instructions (e.g., installation instructions, uninstallation instructions) and control the mechanical arm to transport, install, or uninstall the collimator (e.g., the target collimator or the installed collimator). In some embodiments, the driving mechanism may be configured to communicate with the processing device 120 (or the processor) to receive instructions (e.g., installation instructions, uninstallation instructions) and control the collimator platform to move to change a relative position between the cart 140 and the collimator storage device 160.

In some embodiments, the mechanical arm may include a gripper, a retractable arm, and a sensor. The gripper may be mounted on an end of the retractable arm and configured to grip the collimator (e.g., the target collimator or the installed collimator) during the transport of the collimator. The retractable arm may be configured to stretch and/or contract, and facilitate the transport of the collimator. The sensor may be configured to determine a state of the retractable arm and/or the gripper. For example, the sensor may include an image sensor for capturing an image of the gripper to determine whether the retractable arm moves the gripper to a predetermined location. As another example, the sensor may include a pressure sensor to determine whether the mechanical arm (e.g., the gripper) grips the collimator. The gripper, the retractable arm, and/or the sensor may be configured to communicate with the processing device 120 to receive instructions (e.g., griping instructions, stretching and/or contracting instructions) and control the mechanical arm to transport, install, or uninstall the collimator (e.g., the target collimator or the installed collimator).

The network 150 may include any suitable network that can facilitate the exchange of information and/or data for the automatic collimator installation system 100. In some embodiments, one or more components of the automatic collimator installation system 100 (e.g., the medical device 110, the processing device 120, the storage device 130, the cart 140, the terminal(s) 170, etc.) may communicate information and/or data with one or more other components of the automatic collimator installation system 100 via the network 150. For example, the processing device 120 may obtain an installation instruction or an uninstallation instruction from the terminal(s) 170 via the network 150. As another example, the processing device 120 may instruct the cart 140 to perform one or more operations via the network 150. The network 150 may be and/or include a public network (e.g., the Internet), a private network (e.g., a local area network (LAN), a wide area network (WAN), etc.), a wired network (e.g., an Ethernet network), a wireless network (e.g., a Wi-Fi network), a cellular network (e.g., a Long Term Evolution (LTE) network), a frame relay network, a virtual private network (VPN), a satellite network, a telephone network, routers, hubs, witches, server computers, and/or any combination thereof. For example, the network 150 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 150 may include one or more network access points. For example, the network 150 may include wired and/or wireless network access points such as base stations and/or internet exchange points through which one or more components of the automatic collimator installation system 100 may be connected to the network 150 to exchange data and/or information.

The collimator storage device 160 may be configured to store a plurality of collimators. In some embodiments, the collimator storage device 160 may include a plurality of storage spaces each of which is configured to store a collimator of the plurality of collimators. In some embodiments, the collimator storage device 160 and the medical device 110 may be away from each other. As used herein, the words "away from" refers that the collimator storage device 160 and the medical device 110 are two separate devices, and a distance between the two devices is greater than a distance threshold (e.g., 3 meters). In some embodiments, the collimator storage device 160 may store a large number of collimators. Foe example, a count of the plurality of collimators stored in the collimator storage device 160 may be greater than a count threshold (e.g., 3, 5, etc.).

The terminal(s) 170 may be connected to and/or communicate with the medical device 110, the processing device 120, the storage device 130, and/or the cart 140. In some embodiments, the terminal 170 may include a mobile device 171, a tablet computer 172, a laptop computer 173, or the like, or any combination thereof. For example, the mobile device 171 may include a mobile phone, a personal digital assistant (PDA), a gaming device, a navigation device, a point of sale (POS) device, a laptop, a tablet computer, a desktop, or the like, or any combination thereof. In some embodiments, the terminal 170 may include an input device, an output device, etc. The input device may include alphanumeric and other keys that may be input via a keyboard, a touchscreen (for example, with haptics or tactile feedback), a speech input, an eye tracking input, a brain monitoring system, or any other comparable input mechanism. Other types of the input device may include a cursor control device, such as a mouse, a trackball, or cursor direction keys, etc. The output device may include a display, a printer, or the like, or any combination thereof.

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. However, those variations and modifications do not depart the scope of the present disclosure. In some embodiments, the automatic collimator installation system 100 may include one or more additional components and/or one or more components of the automatic collimator installation system 100 described above may be omitted. Additionally or alternatively, two or more components of the automatic collimator installation system 100 may be integrated into a single component. A component of the automatic collimator installation system 100 may be implemented on two or more sub-components.

Figure 2:
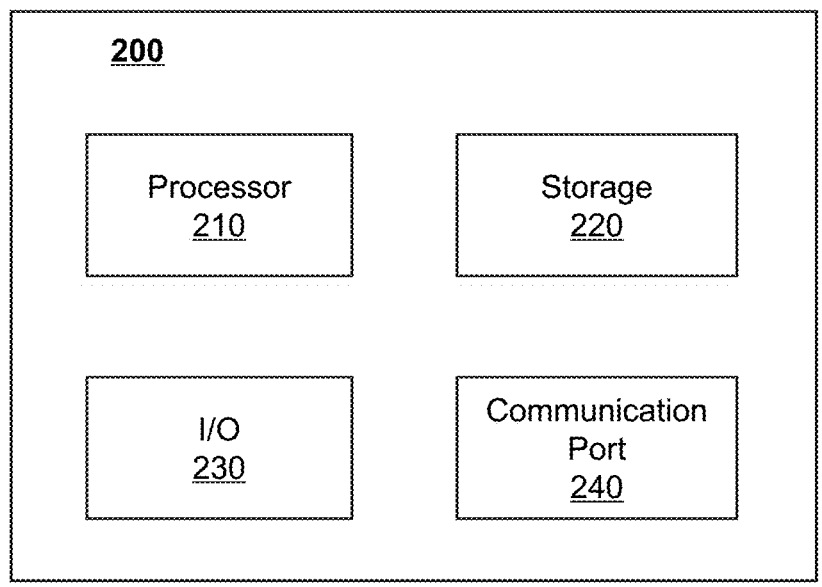
FIG. 2 is a schematic diagram illustrating exemplary hardware and/or software components of an exemplary computing device on which a processing device may be implemented according to some embodiments of the present disclosure.

FIG. 2 is a schematic diagram illustrating exemplary hardware and/or software components of an exemplary computing device on which the processing device 120 may be implemented according to some embodiments of the present disclosure. As illustrated in FIG. 2, a computing device 200 may include a processor 210, a storage 220, an input/output (I/O) 230, and a communication port 240.

The processor 210 may execute computer instructions (e.g., program code) and perform functions of the processing device 120 in accordance with techniques described herein. The computer instructions may include, for example, routines, programs, objects, components, data structures, procedures, modules, and functions, which perform particular functions described herein. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combination thereof.

Merely for illustration, only one processor is described in the computing device 200. However, it should be noted that the computing device 200 in the present disclosure may also include multiple processors. Thus operations and/or method steps that are performed by one processor as described in the present disclosure may also be jointly or separately performed by the multiple processors. For example, if in the present disclosure the processor of the computing device 200 executes both process A and process B, it should be understood that process A and process B may also be performed by two or more different processors jointly or separately in the computing device 200 (e.g., a first processor executes process A and a second processor executes process B, or the first and second processors jointly execute processes A and B).

The storage 220 may store data/information obtained from the medical device 110, the cart 140, the storage device 130, and/or any other component of the automatic collimator installation system 100. The storage 220 may be similar to the storage device 130 described in connection with FIG. 1, and the detailed descriptions are not repeated here.

The I/O 230 may input and/or output signals, data, information, etc. In some embodiments, the I/O 230 may enable a user interaction with the processing device 120. In some embodiments, the I/O 230 may include an input device and an output device. Examples of the input device may include a keyboard, a mouse, a touchscreen, a microphone, a sound recording device, or the like, or a combination thereof. Examples of the output device may include a display device, a loudspeaker, a printer, a projector, or the like, or a combination thereof. Examples of the display device may include a liquid crystal display (LCD), a light-emitting diode (LED)-based display, a flat panel display, a curved screen, a television device, a cathode ray tube (CRT), a touchscreen, or the like, or a combination thereof.

The communication port 240 may be connected to a network (e.g., the network 150) to facilitate data communications. The communication port 240 may establish connections between the processing device 120 and the medical device 110, the cart 140, and/or the storage device 130. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee link, a mobile network link (e.g., 3G, 4G, 5G), or the like, or any combination thereof. In some embodiments, the communication port 240 may be and/or include a standardized communication port, such as RS232, RS485. In some embodiments, the communication port 240 may be a specially designed communication port. For example, the communication port 240 may be designed in accordance with the digital imaging and communications in medicine (DICOM) protocol.

Figure 3:
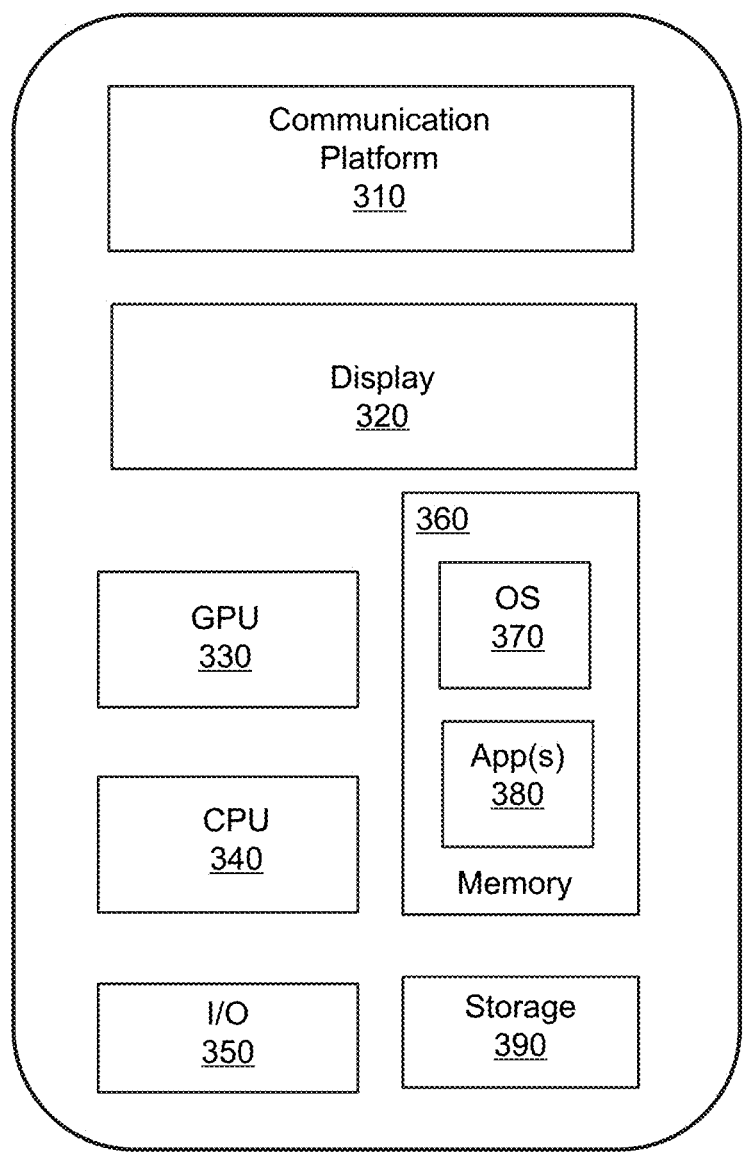
FIG. 3 is a schematic diagram illustrating exemplary hardware and/or software components of an exemplary mobile device according to some embodiments of the present disclosure.

FIG. 3 is a schematic diagram illustrating exemplary hardware and/or software components of an exemplary mobile device according to some embodiments of the present disclosure. In some embodiments, the cart 140, the processing device 120, and/or the terminal(s) 170 may be implemented on a mobile device 300, respectively.

As illustrated in FIG. 3, the mobile device 300 may include a communication platform 310, a display 320, a graphics processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300.

In some embodiments, the communication platform 310 may be configured to establish a connection between the mobile device 300 and other components of the automatic collimator installation system 100, and enable data and/or signal to be transmitted between the mobile device 300 and other components of the automatic collimator installation system 100. For example, the communication platform 310 may establish a wireless connection between the mobile device 300 and the medical device 110, and/or the processing device 120. The wireless connection may include, for example, a Bluetooth™ link, a Wi-Fi™ link, a WiMax™ link, a WLAN link, a ZigBee link, a mobile network link (e.g., 3G, 4G, 5G), or the like, or any combination thereof. The communication platform 310 may also enable the data and/or signal between the mobile device 300 and other components of the automatic collimator installation system 100. For example, the communication platform 310 may transmit data and/or signals inputted by a user to other components of the automatic collimator installation system 100. The inputted data and/or signals may include a user instruction. As another example, the communication platform 310 may receive data and/or signals transmitted from the processing device 120. The received data and/or signals may include imaging data acquired by the medical device 110.

In some embodiments, a mobile operating system (OS) 370 (e.g., iOS™, Android™, Windows Phone™, etc.) and one or more applications (App(s)) 380 may be loaded into the memory 360 from the storage 390 in order to be executed by the CPU 340. The applications 380 may include a browser or any other suitable mobile apps for receiving and rendering information from the processing device 120. User interactions with the information stream may be achieved via the I/O 350 and provided to the processing device 120 and/or other components of the automatic collimator installation system 100 via the network 150.

To implement various modules, units, and their functionalities described in the present disclosure, computer hardware platforms may be used as the hardware platform(s) for one or more of the elements described herein. A computer with user interface elements may be used to implement a personal computer (PC) or another type of work station or terminal device, although a computer may also act as a server if appropriately programmed. It is believed that those skilled in the art are familiar with the structure, programming and general operation of such computer equipment and as a result the drawings should be self-explanatory.

Figure 4:
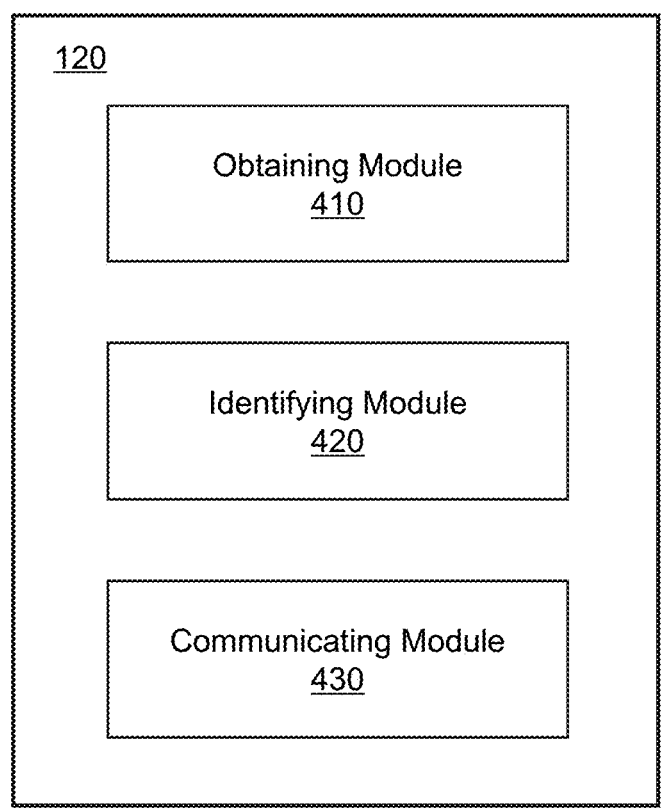
FIG. 4 is a block diagram illustrating an exemplary processing device according to some embodiments of the present disclosure.

FIG. 4 is a block diagram illustrating an exemplary processing device according to some embodiments of the present disclosure. In some embodiments, the processing device 120 may include an obtaining module 410, an identifying module 420, and a control module 430.

The obtaining module 410 may be configured to obtain information. For example, the obtaining module 410 may obtain an instruction (e.g., an installation instruction, an uninstallation instruction, etc.). As another example, the obtaining module 410 may obtain a scan protocol.

The identifying module 420 may be configured to identify, from a plurality of collimators stored in the collimator storage device 160, a target collimator based on the installation instruction.

The control module 430 may be configured to control the cart 140 to transport, install, or uninstall the target collimator. For example, the control module 430 may control the cart 140 to transport the target collimator from the collimator storage device 160 to the medical scanner 111. As another example, the control module 430 may control the cart 140 to align, based on a navigation algorithm, the target collimator with a detector of the medical scanner 111. As still another example, the control module 430 may control the cart 140 to automatically install the target collimator into the medical scanner 111. As still another example, the control module 430 may control the cart 140 to automatically uninstall, using the cart 140, an installed collimator from the medical scanner 111 based on the installation instruction.

It should be noted that the above description of the processing device 120 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more modules may be added or omitted in the processing device 120. For example, the processing device 120 may further include a storage module (not shown in FIG. 4) configured to store data and/or information associated with the automatic collimator installation system 100. In some embodiments, two or more modules may be integrated into a single module. For example, the obtaining module 410 and the control module 430 may be integrated into a single module.

Figure 5:
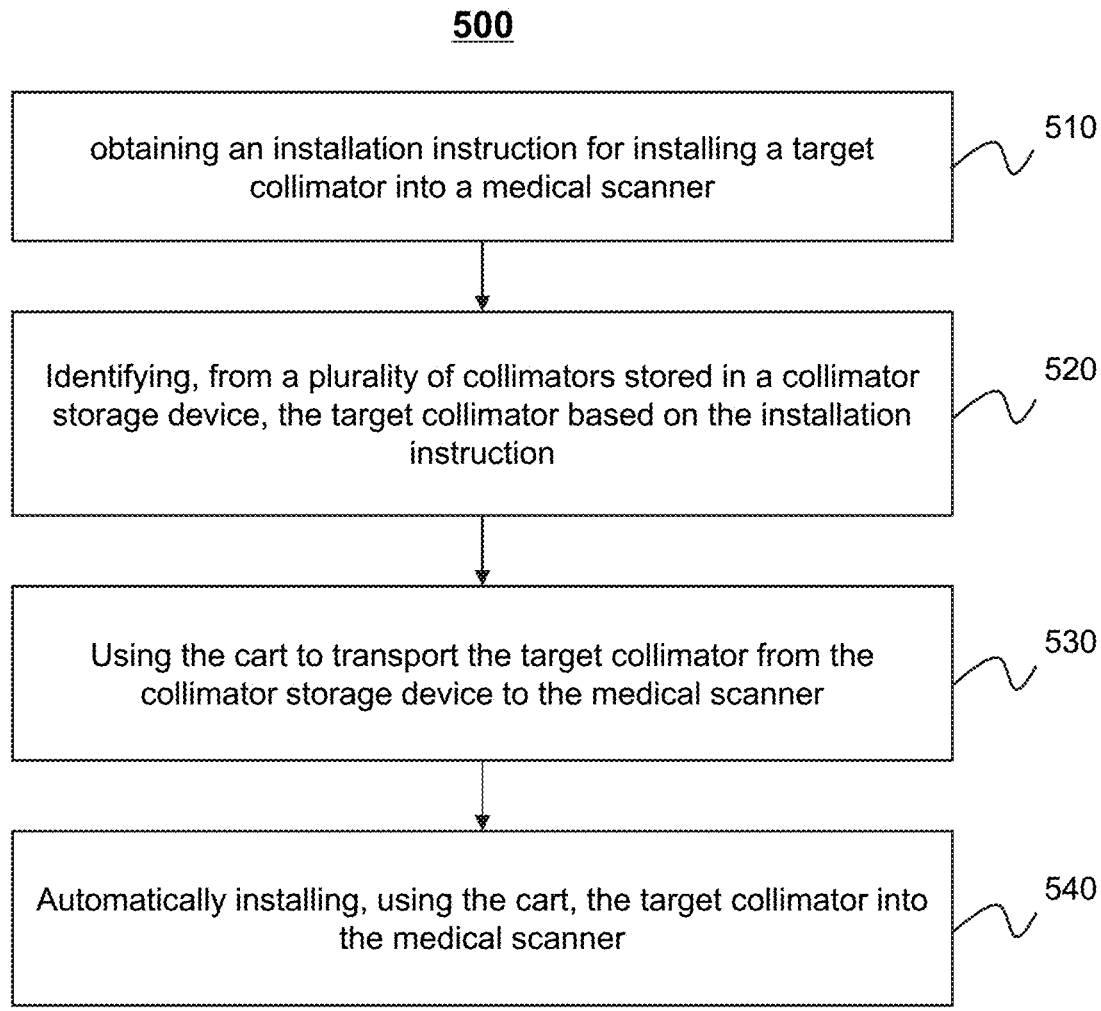
FIG. 5 is a flowchart illustrating an exemplary process for automatically installing a target collimator according to some embodiments of the present disclosure.

FIG. 5 is a flowchart illustrating an exemplary process 500 for automatically installing a target collimator according to some embodiments of the present disclosure. In some embodiments, the process 500 may be implemented in the automatic collimator installation system 100 illustrated in FIG. 1. For example, the process 500 may be stored in the storage device 130 and/or the storage (e.g., the storage 220, the storage 390) as a form of instructions, and invoked and/or executed by the processing device 120 (e.g., the processor 210 of the computing device 200 as illustrated in FIG. 2, the CPU 340 of the mobile device 300 as illustrated in FIG. 3). The operations of the illustrated process presented below are intended to be illustrative. In some embodiments, the process 500 may be accomplished with one or more additional operations not described, and/or without one or more of the operations discussed. Additionally, the order in which the operations of the process 500 as illustrated in FIG. 5 and described below is not intended to be limiting.

In 510, the processing device 120 (e.g., the obtaining module 410) may obtain an installation instruction for installing a target collimator into a medical scanner (e.g., the medical scanner 111).

In some embodiments, the installation instruction may be directly sent from an operator by a terminal device (e.g., the terminal (s) 170, the medical device 110, etc.). The installation instruction may include a target identifier of the target collimator to be installed or an identifier of an installed collimator to be uninstalled, a collimator mode of the target collimator, an energy (e.g., a high energy, a low energy, etc.) of the target collimator, or the like, or any combination thereof. In some embodiments, the collimator mode may include a pinhole collimator, a parallel hole collimator, a fan-beam collimator, a cone-beam collimator, a slit-slat collimator, a conical hole collimator, or the like, or any combination thereof.

In some embodiments, the installation instruction may be determined based on scan protocol. For example, before scanning a subject (e.g., a patient), a scan protocol may be determined. For example, if the scan area of the subject is the chest, a scan protocol corresponding to a chest examination may be obtained. Further, the processing device 120 may determine the installation instruction based on the scan protocol of the subject. In some embodiments, the scan protocol may be previously generated (e.g., manually input by a user or determined by the processing device 120) and stored in a storage device (e.g., the storage device 130). The processing device 120 may retrieve the scan protocol from the storage device, and determine the installation instruction based on the scan protocol. In some embodiments, the scan protocol may be determined based on a contrast agent and/or an activity thereof, a radioactive tracer and/or an activity thereof, a required image quality (e.g., an image resolution, an image signal-to-noise ratio, a sensitivity, etc.), a selection of an operator (e.g., a scan duration, a field of view (FOV), etc.), etc. For example, a size (e.g., a hole size) of the target collimator may be determined based on a required image quality (e.g., an image resolution, a sensitivity, etc.). A collimator mode of the target collimator may be determined based on FOV. An energy (e.g., a high energy, a low energy, etc.) of the target collimator may be determined based on radioactive tracer.

The scan protocol may include, for example, value(s) or value range(s) of scan parameter(s), a portion of the subject to be scanned, feature information of the subject (e.g., the gender, the body shape), a collimator mode of the target collimator to be installed and/or a collimator mode of an installed collimator to be uninstalled, a target identifier of the target collimator to be installed and/or an identifier of an installed collimator to be uninstalled, or the like, or any combination thereof. In some embodiments, the scan parameter(s) may include a scanning mode, a bed position, a voltage of a radiation source, a current of the radiation source, a distance between the radiation source and a detector (also referred to as a source image distance, or a SID), a radiation dose, a scan time, a field of view (FOV), whether to record physiological parameters (e.g., electrocardio (ECG) signal, etc.) synchronously, or the like, or any combination thereof. Merely by way of example, a scan protocol of a myocardial perfusion scanning may include a scanning time of 20 minutes, a single bed, a synchronous recording of ECG signals, a low-energy conical hole collimator, etc. Based on the scan protocol of the myocardial perfusion scanning, the installation instruction may be determined. Correspondingly, the installation instruction may include a conical hole collimator with low energy. More descriptions regarding determining the installation instruction based on the scan protocol may be found elsewhere in the present disclosure. See, e.g., FIG. 12 and the descriptions thereof. In some embodiments, the processing device 120 may send the installation instruction to the cart 140 via the network 150 (e.g., wireless local area network or Bluetooth, etc.). The cart 140 may receive the installation instruction from the processing device 120 and perform an installation process according to the installation instruction.

In 520, the processing device 120 (e.g., the identifying module 420) may identify, from a plurality of collimators stored in the collimator storage device 160, the target collimator based on the installation instruction.

In some embodiments, the collimator storage device 160 may include a plurality of collimators. The plurality of collimators may include different modes of collimators, different energies of collimators, etc. In some embodiments, each collimator may be labeled with an identifier. The identifier may include a mechanical switch, a proximity switch, a photoelectric switch, an electromagnetic sensor, a radiofrequency identification tag, a unique symbol (e.g., a QR code, a bar code, etc.), or the like, or any combination thereof.

In some embodiments, the processing device 120 may identify, from the plurality of collimators stored in the collimator storage device 160, the target collimator based on the installation instruction. For example, the processing device 120 may obtain a target identifier of the target collimator based on the installation instruction. As described above, the installation instruction may include a target identifier of the target collimator to be installed. The processing device 120 may obtain the target identifier of the target collimator from the installation instruction. The processing device 120 may identify a plurality of identifiers respectively corresponding to the plurality of collimators stored in the collimator storage device 160. In some embodiments, the processing device 120 may identify the target collimator based on the plurality of identifiers respectively corresponding to the plurality of collimators. For example, the processing device 120 may identify the target collimator by matching the target identifier with one of the plurality of identifiers respectively corresponding to the plurality of collimators. More descriptions regarding identifying the target collimator may be found elsewhere in the present disclosure. See, e.g., FIG. 10 and the descriptions thereof.

In 530, the processing device 120 (e.g., the control module 430) may use the cart 140 to transport the target collimator from the collimator storage device 160 to the medical scanner 111.

In some embodiments, the processing device 120 may use the cart 140 to grip the target collimator from the collimator storage device 160 and support the target collimator. For example, the mechanical arm (e.g., the gripper) of the cart 140 may grip the target collimator from the collimator storage device 160 after identifying the target collimator. In some embodiments, the processing device 120 may transport, using the retractable arm of the cart 140, the target collimator to the cart body. For example, the processing device 120 may control the gripper to grip the target collimator, and control the retractable arm to extend or retract to transport the target collimator to the cart body. In some embodiments, the cart body (e.g., the collimator platform) may support the target collimator during a transportation process of the target collimator from the collimator storage device 160 to the medical scanner 111.

Figure 6:
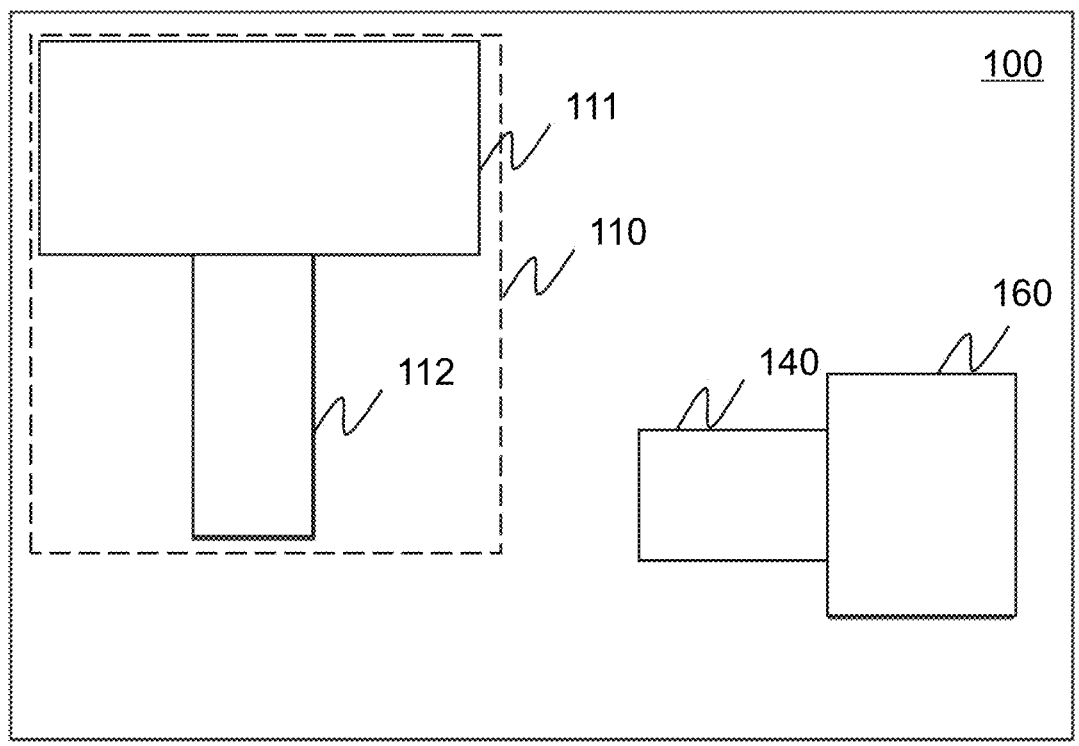
FIG. 6 is a schematic diagram illustrating an exemplary automatic collimator installation system according to some embodiments of the present disclosure.

In some embodiments, to facilitate the automatic installation of the target collimator, the processing device 120 may use the cart 140 (e.g., the wheels of the cart 140) to transport the target collimator from the collimator storage device 160 to a predetermined location of the medical scanner 111. For example, the predetermined location may be close to a detector of the medical scanner 111. FIG. 6 is a schematic diagram illustrating an exemplary automatic collimator installation system 100 according to some embodiments of the present disclosure. As shown in FIG. 6, the medical device 110 may include the medical scanner 111 and the bed 112. During a scanning process of an object, the bed 112 may be configured to support the object and may be close to the medical scanner 111. As shown in FIG. 6, the cart 140 may be close to the collimator storage device 160 to grip the target collimator from the collimator storage device 160. In some embodiments, the collimator storage device 160 and the medical device 110 may be away from each other. As used herein, the words "away from" refers that the collimator storage device 160 and the medical device 110 are two separate devices, and a distance between the two devices is greater than a distance threshold (e.g., 3 meters, 5 meters, etc.). In some embodiments, the collimator storage device 160 and the medical device 110 may be in a same scanning room (e.g., an examination room of a hospital), and the cart 140 may transport the target collimator between the collimator storage device 160 and the medical device 110 in the same scanning room. In some embodiments, the collimator storage device 160 and the medical device 110 may be in separate rooms (e.g., different rooms of a hospital), and the cart 140 may transport the target collimator between the collimator storage device 160 and the medical device 110 in the hospital. For example, the collimator storage device 160 may store collimators of a plurality of medical devices. The cart 140 may transport a collimator (e.g., the target collimator) from the collimator storage device 160 to any one of the medical devices.

Figure 7:
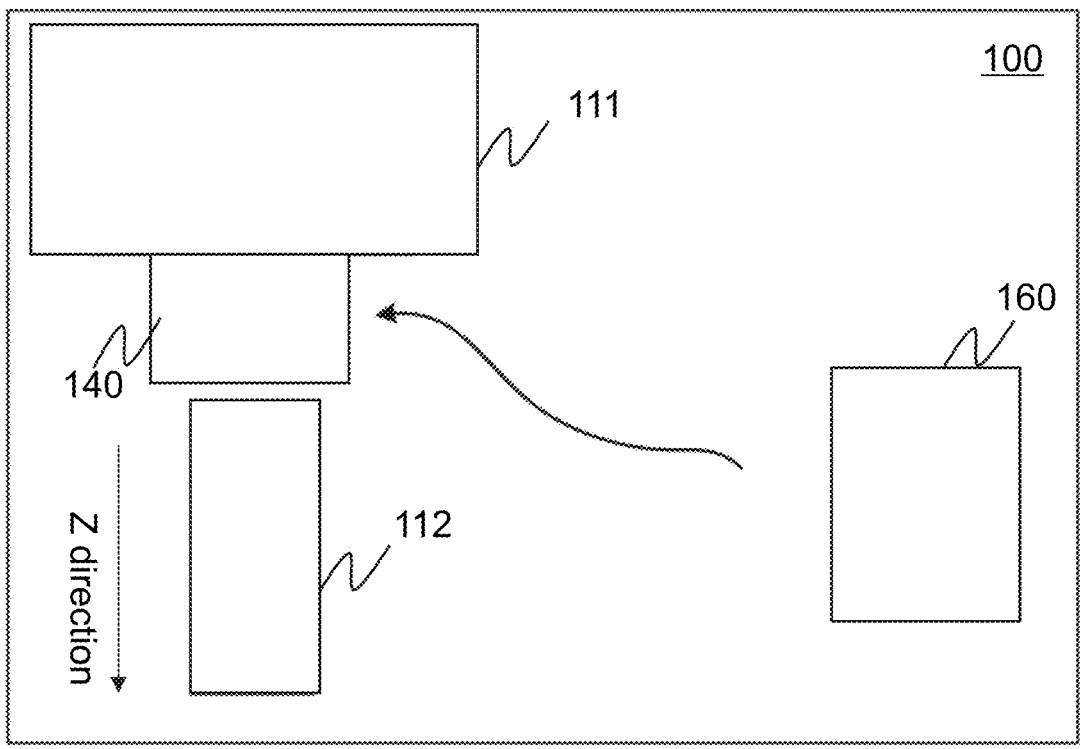
FIG. 7 is a schematic diagram illustrating an exemplary automatic collimator installation system according to some embodiments of the present disclosure.
Figure 8:
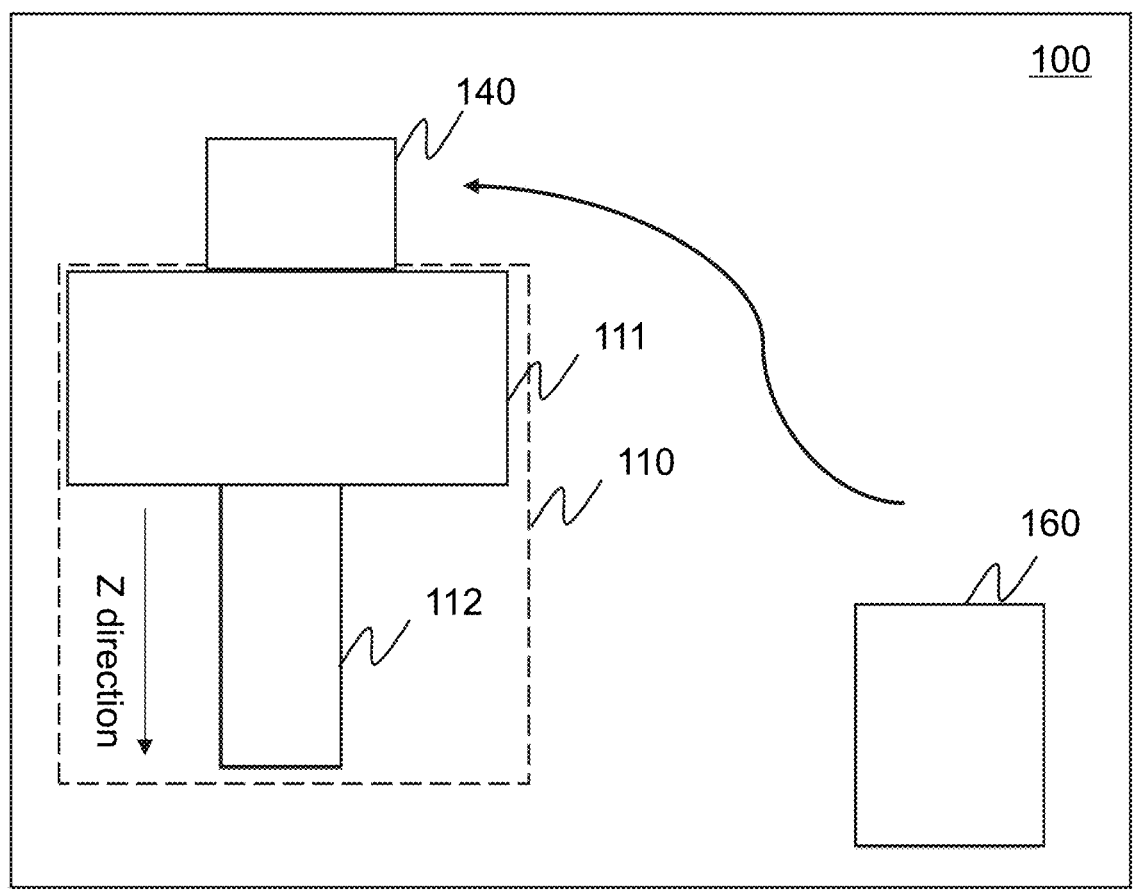
FIG. 8 is a schematic diagram illustrating an exemplary automatic collimator installation system according to some embodiments of the present disclosure.

FIG. 7 is a schematic diagram illustrating an exemplary automatic collimator installation system 100 according to some embodiments of the present disclosure. FIG. 8 is a schematic diagram illustrating an exemplary automatic collimator installation system 100 according to some embodiments of the present disclosure. As shown in FIG. 7, the medical scanner 111 and/or the bed 112 may move relative to each other. After the cart 140 griping the target collimator (as shown in FIG. 6), the bed 112 may move along the direction (e.g., Z direction shown in FIG. 7) in which the bed 112 may move into or out of the gantry of the medical device 111. The cart 140 may transport the target collimator from the collimator storage device 160 to a predetermined location of the medical scanner 111. As shown in FIG. 7, the predetermined location may include a location between the medical scanner 111 and the bed 112 and the predetermined location may be close to the medical scanner 111. Alternatively, as shown in FIG. 8, after the cart 140 griping the target collimator (as shown in FIG. 6), the cart 140 may transport the target collimator from the collimator storage device 160 to a location close to a side of the medical scanner 111 that is away from the bed 112 along the direction (e.g., Z direction shown in FIG. 8) in which the bed 112 may move into or out of the gantry of the medical device 111.

In some embodiments, the processing device 120 may use the cart 140 to transport, based on a predetermined route, the target collimator from the collimator storage device 160 to the predetermined location of the medical scanner 111. In some embodiments, the processing device 120 may use the cart 140 to align, based on a navigation algorithm, the target collimator with a detector of the medical scanner 111. For example, the cart 140 may align the target collimator with a fixture of the detector to facilitate the automatic installation of the target collimator. In some embodiments, an alignment accuracy of the alignment based on the navigation algorithm may be millimeter level. More descriptions regarding transporting and aligning the target collimator may be found elsewhere in the present disclosure. See, e.g., FIG. 9 and the descriptions thereof.

In 540, the processing device 120 (e.g., the control module 430) may automatically install, using the cart 140, the target collimator into the medical scanner 111.

As used herein, the word "automatically" may refer that the installation of the target collimator is performed in a mechanical manner without any human assistance. In some embodiments, the processing device 120 may automatically install, by a locating module of the cart 140, the target collimator onto a detector of the medical scanner 111. In some embodiments, the locating module may include a locating hole, a locating pin, a bolt, a nut, or the like, or any combination thereof. In some embodiments, a locating accuracy of the locating module may be 0.25 millimeter level. For example, the locating module of the cart 140 may include a locating hole, and the medical scanner 111 may include a locating pin that is paired with the locating hole. As another example, the locating module of the cart may include a locating pin, and the medical scanner 111 may include a locating hole that is paired with the locating pin. The locating hole may match with the locating pin, and the processing device 120 may control the gripper of the cart 140 to mount the target collimator onto the medical scanner 111. In some embodiments, the target collimator may be installed by fixedly connecting with the detector of the medical scanner 111.

In some embodiments, before installing the target collimator, the medical scanner 111 may include an installed collimator that is pre-installed thereon. The processing device 120 may automatically uninstall the installed collimator before installing the target collimator. For example, the processing device 120 may automatically uninstall, using the cart 140, the installed collimator from the medical scanner 111 based on the installation instruction. For example, after the cart 140 transports the target collimator to the predetermined location of the medical scanner 111 and before installing the target collimator, the processing device 120 may control the cart 140 to uninstall the installed collimator. For example, the gripper of the cart 140 may grip the installed collimator and transport the installed collimator from the medical scanner 111 to the cart 140 (e.g., the installed collimator may be transported to the collimator platform of the cart 140). In some embodiments, the processing device 120 may use the cart 140 to transport the installed collimator from the medical scanner 111 to the collimator storage device 160. For example, after uninstalling the installed collimator and installing the target collimator, the cart 140 may transport the installed collimator to the collimator storage device 160. In some embodiments, the installation of the target collimator and the uninstallation of the installed collimator may be performed by a same cart 140. Alternative, the installation of the target collimator and the uninstallation of the installed collimator may be performed by two different carts 140. For example, one cart may be configured to install the target collimator, and the other cart may be configured to uninstall the installed collimator. More descriptions regarding uninstalling the installed collimator may be found elsewhere in the present disclosure. See, e.g., FIG. 11 and the descriptions thereof.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, one or more operations may be added into the process 500. For example, before operation 540 for automatically installing the target collimator, an uninstallation process of the installed collimator may be performed.

Figure 9:
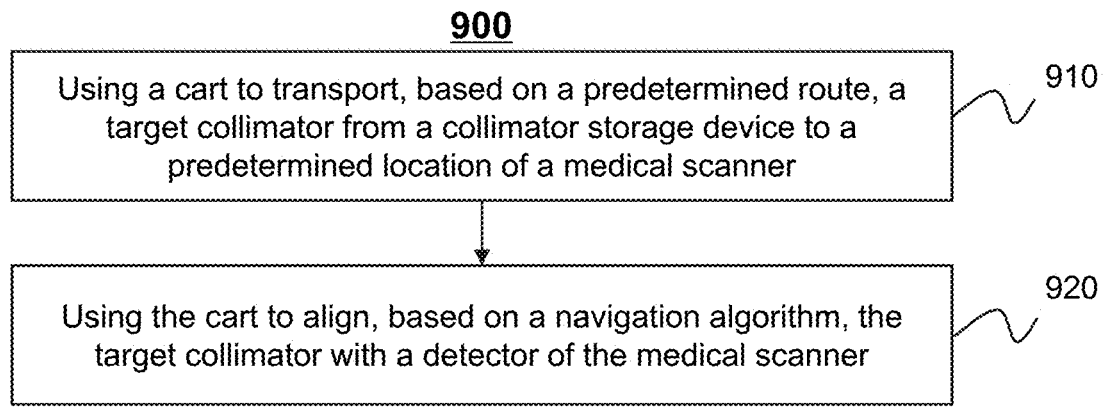
FIG. 9 is a flowchart illustrating an exemplary process for transporting a target collimator according to some embodiments of the present disclosure.

FIG. 9 is a flowchart illustrating an exemplary process 900 for transporting a target collimator according to some embodiments of the present disclosure. In some embodiments, the process 900 may be implemented in the automatic collimator installation system 100 illustrated in FIG. 1. For example, the process 900 may be stored in the storage device 130 and/or the storage (e.g., the storage 220, the storage 390) as a form of instructions, and invoked and/or executed by the processing device 120 (e.g., the processor 210 of the computing device 200 as illustrated in FIG. 2, the CPU 340 of the mobile device 300 as illustrated in FIG. 3). The operations of the illustrated process presented below are intended to be illustrative. In some embodiments, the process 900 may be accomplished with one or more additional operations not described, and/or without one or more of the operations discussed. Additionally, the order in which the operations of the process 900 as illustrated in FIG. 9 and described below is not intended to be limiting. In some embodiments, operation 530 may be performed according to process 900.

In 910, the processing device 120 (e.g., the control module 430) may use the cart 140 to transport, based on a predetermined route, the target collimator from the collimator storage device 160 to a predetermined location of the medical scanner 111.

In some embodiments, the collimator storage device 160 and the medical scanner 111 may be located at two relative fixed positions. The predetermined route between the collimator storage device 160 and the medical scanner 111 may be predetermined and stored in a storage device (e.g., the storage device 130) or the cart 140. For example, the predetermined route may be determined by an operator of the automatic collimator installation system 100 and transmit to the storage device or the cart 140. As another example, the predetermined route may be determined by the processing device 120 based on an indoor wireless positioning technologies. Exemplary indoor wireless positioning technologies may include Wi-Fi positioning technology, Bluetooth positioning technology, infrared positioning technology, ultra-wideband positioning technology, RFID positioning technology, ZigBee positioning technology, motion capture positioning technology, ultrasonic positioning technology, or the like, or any combination thereof. In some embodiments, the processing device 120 may retrieve the predetermined route from the storage device, and transport, based on the predetermined route, the target collimator from the collimator storage device 160 to the predetermined location of the medical scanner 111. In some embodiments, the cart 140 may store the predetermined route, and once obtaining an installation instruction, the cart 140 may directly transport the target collimator based on the predetermined route to improve an efficiency for obtaining the predetermined route. In some embodiments, the predetermined route may be included in the installation instruction. The processing device 120 may parse the installation instruction and send the predetermined route to the cart 140. The cart 140 may obtain the predetermined route to transport the target collimator. In some embodiments, the predetermined location may be a location that facilitate the installation of the target collimator. More descriptions regarding the predetermined location may be found elsewhere in the present disclosure. See, e.g., FIGS. 5, 7, and 8 and the descriptions thereof.

In 920, the processing device 120 (e.g., the control module 430) may use the cart 140 to align, based on a navigation algorithm, the target collimator with a detector of the medical scanner 111.

In some embodiment, an alignment accuracy of the alignment based on the navigation algorithm may be millimeter level. Exemplary navigation algorithm may include a laser navigation algorithm, a visual navigation algorithm, an inertial navigation algorithm, or the like, or any combination thereof. In some embodiments, the navigation algorithm may be stored in a storage device (e.g., the storage device 130), and the processing device 120 may retrieve the navigation algorithm from the storage device, and control the cart 140 to align the target collimator based on the navigation algorithm. In some embodiments, the cart 140 may align the target collimator with a fixture (e.g., a groove, a pin, etc.) of the detector to facilitate the automatic installation of the target collimator. For example, the cart 140 may include an image sensor for capturing an image of the detector of the medical scanner 111. The cart 140 may align the target collimator with the detector based on the image captured from the image sensor.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Figure 10:
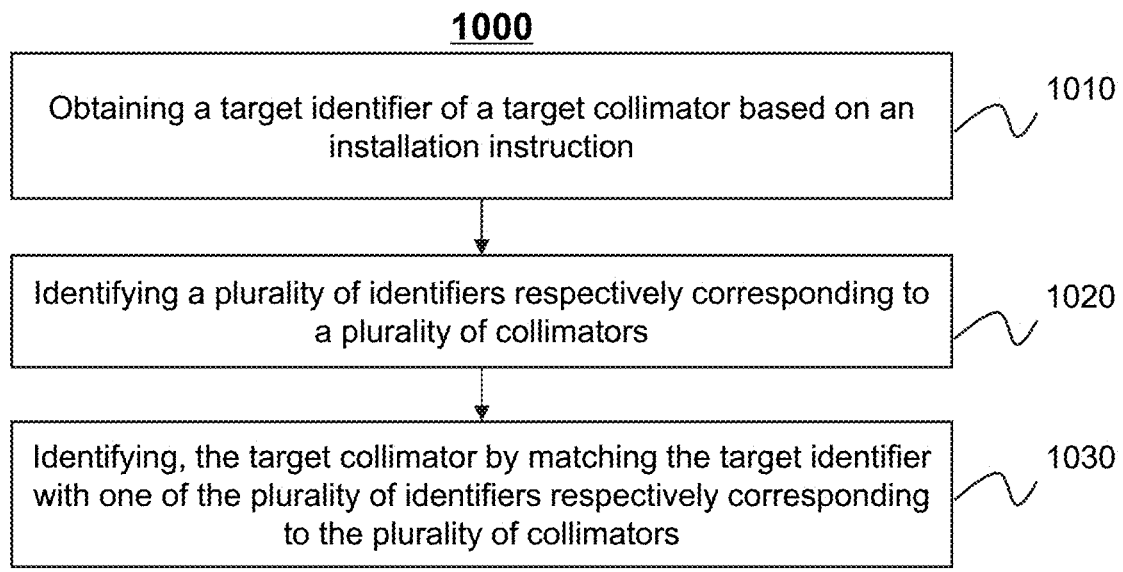
FIG. 10 is a flowchart illustrating an exemplary process for identifying a target collimator according to some embodiments of the present disclosure.

FIG. 10 is a flowchart illustrating an exemplary process 1000 for identifying a target collimator according to some embodiments of the present disclosure. In some embodiments, the process 1000 may be implemented in the automatic collimator installation system 100 illustrated in FIG. 1. For example, the process 1000 may be stored in the storage device 130 and/or the storage (e.g., the storage 220, the storage 390) as a form of instructions, and invoked and/or executed by the processing device 120 (e.g., the processor 210 of the computing device 200 as illustrated in FIG. 2, the CPU 340 of the mobile device 300 as illustrated in FIG. 3). The operations of the illustrated process presented below are intended to be illustrative. In some embodiments, the process 1000 may be accomplished with one or more additional operations not described, and/or without one or more of the operations discussed. Additionally, the order in which the operations of the process 1000 as illustrated in FIG. 10 and described below is not intended to be limiting. In some embodiments, operation 520 may be performed according to process 1000.

In 1010, the processing device 120 (e.g., the identifying module 420) may obtain a target identifier of the target collimator based on the installation instruction. In some embodiments, the installation instruction may include a target identifier of the target collimator to be installed, and the processing device 120 may parse the installation instruction to obtain the target identifier of the target collimator.

In 1020, the processing device 120 (e.g., the identifying module 420) may identify a plurality of identifiers respectively corresponding to the plurality of collimators.

In some embodiments, each of the plurality of collimators stored in the collimator storage device 160 may be labeled with an identifier. The identifier may include a mechanical switch (e.g., a contact switch), a proximity switch, a photoelectric switch (e.g., a photoelectric correlated cell), an electromagnetic sensor (e.g., a Hall element), a radiofrequency identification tag, a unique symbol (e.g., a QR code, a bar code, etc.), or the like, or any combination thereof. For example, each of the plurality of collimators may be labeled with a QR code. The cart 140 (e.g., a sensor of the cart 140) may scan the QR codes of the plurality of collimators to identify the plurality of identifiers respectively corresponding to the plurality of collimators. In some embodiments, each of the plurality of collimators may be stored at a fixed storage space of the collimator storage device 160. Once the cart 140 finishes scanning the QR codes of the plurality of collimators, a mapping relationship between a QR code of a collimator and a corresponding storage space that stores the collimator may be stored in a storage device (e.g., the storage device 130). Each time the processing device 120 obtains an installation instruction, the processing device 120 may access the storage device to obtain a storage space that stores a required collimator. The cart 140 may grip the required collimator from the storage space of the collimator storage device 160. In this way, scanning all of the QR codes of the plurality of collimators each time when the processing device 120 obtains an installation instruction may be avoided, thereby saving an identify time for identifying the collimators.

In 1030, the processing device 120 (e.g., the identifying module 420) may identify the target collimator by matching the target identifier with one of the plurality of identifiers respectively corresponding to the plurality of collimators.

In some embodiments, the processing device 120 may match the target identifier with one of the plurality of identifiers respectively corresponding to the plurality of collimators. For example, a mechanical switch (e.g., a contact switch) may be triggered by the processing device 120, and a collimator being connected to the mechanical switch may be identified as the target collimator. As another example, the target collimator may be labeled with a target QR code. The processing device 120 may scan QR codes of the plurality of collimators, and identify a collimator with a QR code that is same with the target QR code as the target collimator. In some embodiments, if there is no identifier matching with the target identifier, the processing device 120 may generate a notice indicating that there is no target collimator in the collimator storage device 160.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

FIG. 11 is a flowchart illustrating an exemplary process 1100 for uninstalling an installed collimator according to some embodiments of the present disclosure. In some embodiments, the process 1100 may be implemented in the automatic collimator installation system 100 illustrated in FIG. 1. For example, the process 1100 may be stored in the storage device 130 and/or the storage (e.g., the storage 220, the storage 390) as a form of instructions, and invoked and/or executed by the processing device 120 (e.g., the processor 210 of the computing device 200 as illustrated in FIG. 2, the CPU 340 of the mobile device 300 as illustrated in FIG. 3). The operations of the illustrated process presented below are intended to be illustrative. In some embodiments, the process 1100 may be accomplished with one or more additional operations not described, and/or without one or more of the operations discussed. Additionally, the order in which the operations of the process 1100 as illustrated in FIG. 11 and described below is not intended to be limiting.

In 1110, the processing device 120 (e.g., the control module 430) may automatically uninstall, using the cart 140, an installed collimator from the medical scanner based on the installation instruction.

In some embodiments, before installing the target collimator, the medical scanner 111 may include an installed collimator that is pre-installed thereon. The processing device 120 may automatically uninstall the installed collimator before installing the target collimator. For example, the processing device 120 may automatically uninstall, using the cart 140, the installed collimator from the medical scanner 111 based on the installation instruction. For example, after the cart 140 transports the target collimator to the predetermined location of the medical scanner 111 and before installing the target collimator, the processing device 120 may control the cart 140 to uninstall the installed collimator. For example, the gripper of the cart 140 may grip the installed collimator and transport the installed collimator from the medical scanner 111 to the cart 140. For example, the installed collimator may be transported to the collimator platform of the cart 140.

In some embodiments, the installation instruction may include determining whether there is an installed collimator pre-installed on the medical scanner 111. In response to determining that there is an installed collimator that is pre-installed on the medical scanner 111, the processing device 120 may control the cart 140 to uninstall the installed collimator before installing the target collimator. In response to determining that there is not an installed collimator that is pre-installed on the medical scanner 111, the processing device 120 may control the cart 140 to directly install the target collimator. In some embodiments, the cart 140 may include a sensor (e.g., an image sensor) to determine whether there is an installed collimator.

In 1120, the processing device 120 (e.g., the control module 430) may use the cart 140 to transport the installed collimator from the medical scanner 111 to the collimator storage device 160.

In some embodiments, the processing device 120 may use the cart 140 to transport the installed collimator from the medical scanner 111 to the collimator storage device 160. For example, after uninstalling the installed collimator and installing the target collimator, the cart 140 may transport the installed collimator to the collimator storage device 160. In some embodiments, the processing device 120 may identify the installed collimator to obtain an identifier of the installed collimator, and control the cart 140 to store the installed collimator into the collimator storage device 160. For example, the processing device 120 may access the storage device (e.g., the storage device 130) to obtain a mapping relationship between the identifiers of the plurality of collimators and the storage spaces. The processing device 120 may control the cart 140 to store the installed collimator into a corresponding storage space of the collimator storage device 160 based on the mapping relationship.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

FIG. 12 is a flowchart illustrating an exemplary process 1200 for determining an installation instruction according to some embodiments of the present disclosure. In some embodiments, the process 1200 may be implemented in the automatic collimator installation system 100 illustrated in FIG. 1. For example, the process 1200 may be stored in the storage device 130 and/or the storage (e.g., the storage 220, the storage 390) as a form of instructions, and invoked and/or executed by the processing device 120 (e.g., the processor 210 of the computing device 200 as illustrated in FIG. 2, the CPU 340 of the mobile device 300 as illustrated in FIG. 3). The operations of the illustrated process presented below are intended to be illustrative. In some embodiments, the process 1200 may be accomplished with one or more additional operations not described, and/or without one or more of the operations discussed. Additionally, the order in which the operations of the process 1200 as illustrated in FIG. 12 and described below is not intended to be limiting. In some embodiments, operation 510 may be performed according to process 1200.

In 1210, the processing device 120 (e.g., the obtaining module 410) may obtain a scan protocol.

In some embodiments, the scan protocol may include, for example, value(s) or value range(s) of scan parameter(s), a portion of the subject to be scanned, feature information of the subject (e.g., the gender, the body shape), a collimator mode of the target collimator to be installed and/or a collimator mode of an installed collimator to be uninstalled, a target identifier of the target collimator to be installed and/or an identifier of an installed collimator to be uninstalled, or the like, or any combination thereof. In some embodiments, the scan parameter(s) may include a scanning mode, a bed position, a voltage of a radiation source, a current of the radiation source, a distance between the radiation source and a detector (also referred to as a source image distance, or a SID), a radiation dose, a scan time, a field of view (FOV), whether to record physiological parameters (e.g., electrocardio (ECG) signal, etc.) synchronously, or the like, or any combination thereof. In some embodiments, the processing device 120 may obtain the scan protocol from an input of an operator of the automatic collimator installation system 100. In some embodiments, the processing device 120 may obtain scan parameter(s) input by the operator of the automatic collimator installation system 100, and generate the scan protocol based on the scan parameter(s).

In some embodiments, the scan protocol may be previously generated (e.g., manually input by a user or determined by the processing device 120) and stored in a storage device (e.g., the storage device 130). The processing device 120 may retrieve the scan protocol from the storage device. In some embodiments, the scan protocol may be determined based on a contrast agent and/or an activity thereof, a radioactive tracer and/or an activity thereof, a required image quality (e.g., an image resolution, an image signal-to-noise ratio, a sensitivity, etc.), a selection of an operator (e.g., a scan duration, a field of view (FOV), etc.), etc. For example, a size (e.g., a hole size) of the target collimator may be determined based on a required image quality (e.g., an image resolution, a sensitivity, etc.). A collimator mode of the target collimator may be determined based on FOV. An energy (e.g., a high energy, a low energy, etc.) of the target collimator may be determined based on radioactive tracer.

In 1220, the processing device 120 (e.g., the obtaining module 410) may determine the installation instruction based on the scan protocol.

As described above, the scan protocol may include a collimator mode of the target collimator to be installed and/or a collimator mode of an installed collimator to be uninstalled, a target identifier of the target collimator to be installed and/or an identifier of an installed collimator to be uninstalled, etc. The processing device 120 may determine the installation instruction based on the scan protocol. For example, the installation instruction may include a target identifier of the target collimator to be installed or an identifier of an installed collimator to be uninstalled, a collimator mode of the target collimator, an energy (e.g., a high energy, a low energy, etc.) of the target collimator, or the like, or any combination thereof.

Merely by way of example, a scan protocol of a myocardial perfusion scanning may include a scanning time of 20 minutes, a single bed, a synchronous recording of ECG signals, a low-energy conical hole collimator, etc. Based on the scan protocol of the myocardial perfusion scanning, the installation instruction may be determined. Correspondingly, the installation instruction may include a conical hole collimator with low energy.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "module," "unit," "component," "device," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claim subject matter lie in less than all features of a single foregoing disclosed embodiment.

What is claimed is:

1. An automatic collimator installation system, comprising a cart, a storage medium including a set of instructions, and at least one processor configured to communicate with the storage medium, wherein when executing the set of instructions, the at least one processor is configured to direct the system to perform operations including:

obtaining an installation instruction for installing a target collimator into a medical scanner;

identifying, from a plurality of collimators stored in a collimator storage device, the target collimator based on the installation instruction;

using the cart to transport the target collimator from the collimator storage device to the medical scanner; and automatically installing, using the cart, the target collimator into the medical scanner.

2. The automatic collimator installation system of claim 1, wherein the using the cart to transport the target collimator from the collimator storage device to the medical scanner includes:

using the cart to transport, based on a predetermined route, the target collimator from the collimator storage device to a predetermined location of the medical scanner; and using the cart to align, based on a navigation algorithm, the target collimator with a detector of the medical scanner.

3. The automatic collimator installation system of claim 2, wherein the navigation algorithm includes at least one of: a laser navigation algorithm, a visual navigation algorithm, or an inertial navigation algorithm.

4. The automatic collimator installation system of claim 1, wherein the automatically installing, by the cart, the target collimator into the medical scanner includes:

automatically installing, by a locating module of the cart, the target collimator onto a detector of the medical scanner.

5. The automatic collimator installation system of claim 4, wherein the locating module includes a locating hole or a locating pin.

6. The automatic collimator installation system of claim 1, wherein the identifying, from the plurality of collimators stored in the collimator storage device, the target collimator based on the installation instruction includes:

obtaining a target identifier of the target collimator based on the installation instruction;

identifying a plurality of identifiers respectively corresponding to the plurality of collimators; and identifying the target collimator by matching the target identifier with one of the plurality of identifiers respectively corresponding to the plurality of collimators.

7. The automatic collimator installation system of claim 6, wherein the plurality of identifiers of the plurality of collimators is identified according to at least one of: a mechanical switch, a proximity switch, a photoelectric switch, an electromagnetic sensor, a radiofrequency identification tag, or a unique symbol.

8. The automatic collimator installation system of claim 1, wherein the operations further includes:

automatically uninstalling, using the cart, an installed collimator from the medical scanner based on the installation instruction; and using the cart to transport the installed collimator from the medical scanner to the collimator storage device.

9. The automatic collimator installation system of claim 1, wherein the target collimator includes at least one of: a pinhole collimator, a parallel hole collimator, a fan-beam collimator, a cone-beam collimator, or a slit-slat collimator.

10. The automatic collimator installation system of claim 1, further comprising the collimator storage device configured to store the plurality of collimators, wherein the collimator storage device is away from the medical scanner.

11. The automatic collimator installation system of claim 1, wherein the operations further includes:

obtaining a scan protocol; and determining the installation instruction based on the scan protocol.

12. A cart, comprising a mechanical arm, a cart body, a processor, and a storage medium including a set of instructions, the processor configured to communicate with the storage medium, wherein when executing the set of instructions, the processor is configured to direct the cart to perform operations including:

obtaining an installation instruction for installing a target collimator into a medical scanner;

identifying, from a plurality of collimators stored in a collimator storage device, the target collimator based on the installation instruction;

griping, using the mechanical arm, the target collimator from the collimator storage device to the cart body;

controlling the cart body to transport the target collimator from the collimator storage device to the medical scanner; and automatically installing, using the mechanical arm, the target collimator into the medical scanner.

13. The cart of claim 12, wherein the cart body includes:

a collimator platform configured to support the target collimator; and a driving mechanism mounted on the collimator platform, wherein the driving mechanism is configured to receive installation instructions and control the collimator platform to move to change a relative position between the cart and the collimator storage device.

14. The cart of claim 12, wherein the mechanical arm includes:

a retractable arm configured to stretch or contract to transport the target collimator; and a gripper mounted on the retractable arm, wherein the gripper is configured to grip the target collimator.

15. The cart of claim 12, further comprising a pressure sensor configured to determine whether the mechanical arm grips the target collimator.

16. An automatic collimator installation method, comprising:

obtaining an installation instruction for installing a target collimator into a medical scanner;

identifying, from a plurality of collimators stored in a collimator storage device, the target collimator based on the installation instruction;

using a cart to transport the target collimator from the collimator storage device to the medical scanner; and automatically installing, using the cart, the target collimator into the medical scanner.

17. The automatic collimator installation method of claim 16, wherein the using the cart to transport the target collimator from the collimator storage device to the medical scanner includes:

using the cart to transport, based on a predetermined route, the target collimator from the collimator storage device to a predetermined location of the medical scanner; and using the cart to align, based on a navigation algorithm, the target collimator with a detector of the medical scanner.

18. The automatic collimator installation method of claim 16, wherein the automatically installing, by the cart, the target collimator into the medical scanner includes:

automatically installing, by a locating module of the cart, the target collimator onto a detector of the medical scanner.

19. The automatic collimator installation method of claim 16, wherein the identifying, from the plurality of collimators stored in the collimator storage device, the target collimator based on the installation instruction includes:
- obtaining a target identifier of the target collimator based on the installation instruction;
- identifying a plurality of identifiers respectively corresponding to the plurality of collimators; and
- identifying the target collimator by matching the target identifier with one of the plurality of identifiers respectively corresponding to the plurality of collimators.

20. The automatic collimator installation method of claim 16, further comprising:
- automatically uninstalling, using the cart, an installed collimator from the medical scanner based on the installation instruction; and
- using the cart to transport the installed collimator from the medical scanner to the collimator storage device.

* * * * *